United States Patent [19]
Mitragotri et al.

[11] Patent Number: 6,002,961
[45] Date of Patent: *Dec. 14, 1999

[54] TRANSDERMAL PROTEIN DELIVERY USING LOW-FREQUENCY SONOPHORESIS

[75] Inventors: Samir S. Mitragotri, Cambridge; Daniel Blankschtein, Brookline; Robert S. Langer, Newton, all of Mass.

[73] Assignee: Massachusetts Institute of Technology, Cambridge, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/507,060

[22] Filed: Jul. 25, 1995

[51] Int. Cl.⁶ ................................ A61B 17/00
[52] U.S. Cl. .................. 604/20; 604/2; 424/448; 424/449
[58] Field of Search .................. 604/20; 601/2; 424/448, 449

[56] References Cited

U.S. PATENT DOCUMENTS

| | | | |
|---|---|---|---|
| 3,551,554 | 12/1970 | Herschler | 424/7 |
| 3,711,602 | 1/1973 | Herschler | 424/45 |
| 3,711,606 | 1/1973 | Herschler | 424/243 |
| 4,002,221 | 1/1977 | Buchalter | 181/0.5 |
| 4,127,125 | 11/1978 | Takemoto et al. | 128/172.1 |
| 4,144,646 | 3/1979 | Takemoto et al. | 32/40 R |
| 4,176,664 | 12/1979 | Kalish | 128/156 |
| 4,249,531 | 2/1981 | Hiller et al. | 128/260 |
| 4,280,494 | 7/1981 | Cosgrove, Jr. et al. | 128/213 R |
| 4,309,989 | 1/1982 | Fahim | 128/24 A |
| 4,372,296 | 2/1983 | Fahim | 128/24 |
| 4,537,776 | 8/1985 | Cooper | 514/424 |
| 4,557,943 | 12/1985 | Rosler et al. | 427/38 |
| 4,563,184 | 1/1986 | Korol | 604/368 |

(List continued on next page.)

FOREIGN PATENT DOCUMENTS

| | | | |
|---|---|---|---|
| 0 043 738 B1 | 10/1985 | European Pat. Off. | A61K 9/06 |
| 386408 | 5/1990 | European Pat. Off. | |
| 612525 | 8/1994 | European Pat. Off. | |
| 27 56 460 | 6/1979 | Germany | A61M 37/00 |
| 3-170172 | 7/1991 | Japan | A61N 1/30 |
| 445433 | 11/1974 | U.S.S.R. | |
| 556805 | 6/1977 | U.S.S.R. | |
| 591186 | 1/1978 | U.S.S.R. | |
| 0910157 | 2/1978 | U.S.S.R. | |
| 506421 | 2/1978 | U.S.S.R. | |
| 1 577 551 | 2/1976 | United Kingdom | |
| 2153223 | 8/1985 | United Kingdom | A61K 47/00 |
| 88/0000 | 11/1988 | WIPO | |
| 90/01971 | 3/1990 | WIPO | |
| 91/12772 | 9/1991 | WIPO | A61B 17/00 |
| 93/20745 | 10/1993 | WIPO | A61B 5/00 |

OTHER PUBLICATIONS

Egorov, E.A. et al.,. "use of the Variants of the Pharmacophysical Influence in Ophthalmology", 102 Ophthamology Journal #2 (1992).

Eppstein, D.A. et al.,"Applications of Liposome Formulations for Antimicrobial/Antiviral Therapy" Liposomes as Drug Carriers 311, 315 (G. Gregoriadis ed. 1988).

Eppstein, D.A., "Medical Utility of Interferons: Approaches to Increasing Therapeutic Efficacy" 7 Pharmacy International 195–198 (1986).

(List continued on next page.)

*Primary Examiner*—Raj Bawa
*Attorney, Agent, or Firm*—Arnall Golden & Gregory, LLP

[57] ABSTRACT

Applications of low-frequency (20 KHz) ultrasound enhances transdermal transport of high-molecular weight proteins. This method includes a simultaneous application of ultrasound and protein on the skin surface in order to deliver therapeutic doses of proteins across the skin. Examples demonstrate in vitro and in vivo administration of insulin (molecular weight 6,000 D), and in vitro administration of gamma interferon (molecular weight 17,000 D), and erythropoeitin (molecular weight 48,000 D).

6 Claims, 3 Drawing Sheets

U.S. PATENT DOCUMENTS

| | | | |
|---|---|---|---|
| 4,646,725 | 3/1987 | Moasset | 128/24 A |
| 4,698,058 | 10/1987 | Greenfeld et al. | 604/266 |
| 4,767,402 | 8/1988 | Kost | 604/22 |
| 4,780,212 | 10/1988 | Kost et al. | 210/646 |
| 4,787,888 | 11/1988 | Fox | 604/20 |
| 4,820,720 | 4/1989 | Sanders et al. | 514/356 |
| 4,821,740 | 4/1989 | Tachibana et al. | 128/798 |
| 4,834,978 | 5/1989 | Nuwayser | 424/448 |
| 4,855,298 | 8/1989 | Yamada et al. | 514/259 |
| 4,860,058 | 8/1989 | Kobayashi et al. | 355/27 |
| 4,863,970 | 9/1989 | Patel et al. | 514/784 |
| 4,953,565 | 9/1990 | Tachibana et al. | 128/798 |
| 5,006,342 | 4/1991 | Cleary et al. | 424/445 |
| 5,007,438 | 4/1991 | Tachibana | 128/798 |
| 5,016,615 | 5/1991 | Driller | 128/24 |
| 5,076,273 | 12/1991 | Schoendorfer et al. | 128/632 |
| 5,115,805 | 5/1992 | Bommannan et al. | 128/24 AA |
| 5,139,023 | 8/1992 | Stanley et al. | 128/637 |
| 5,140,985 | 8/1992 | Schroder et al. | 128/632 |
| 5,171,215 | 12/1992 | Flanagan | 604/22 |
| 5,197,946 | 3/1993 | Tachibana | 604/22 |
| 5,231,975 | 8/1993 | Bommannan et al. | 128/24 AA |
| 5,267,985 | 12/1993 | Shimada | 604/290 |
| 5,315,998 | 5/1994 | Tachibana et al. | 128/660.01 |
| 5,323,769 | 6/1994 | Bommannan et al. | 601/2 |
| 5,386,837 | 2/1995 | Sterzer | 128/898 |
| 5,401,237 | 3/1995 | Tachibana et al. | 604/4 |
| 5,405,614 | 4/1995 | D'Angelo et al. | 424/449 |
| 5,415,629 | 5/1995 | Henley | 604/20 |
| 5,421,816 | 6/1995 | Lipkovker | 604/20 |
| 5,445,611 | 8/1995 | Eppstein et al. | 604/49 |
| 5,458,140 | 10/1995 | Eppstein et al. | 128/632 |

OTHER PUBLICATIONS

Eppstein, D.A. et al., "Alternative Delivery Systems for Peptides and Proteins as Drugs" 5 CRC Reviews in Therapeutic Drug Carrier Systems 99, 125 (1988).

Ulashik, V.S. et al., Ultrasound Therapy (Minsk, Belarus 1983).

Apfel, R.E., Possibility of Microcavitation from Diagnostic Ultrasound, *IEEE Trans. Ultrason. Ferroelectronics Freq. Control UFFC*–33:139–142 (1986).

Aungst et al., "Contributions of Drug Solubilization, Partioning, Barrier Disruption, and Solvent Permeation to the Enhancement of Skin Permeation of Various Compounds with Fatty Acids and Amines," *Pharm. Res.* 7:712–718 (1990).

Barry, "Mode of Action of Penetration Enhancers in Human Skin," *J. Controlled Rel.* 6:85–97 (1987).

Bommer, et al., "Subcutaneous Erythropoeitin," *Lancet* 406 (1988).

Burnette, R. R., "Iontophoresis," *Transdermal Drug Delivery Developmental Issues and Research Initiatives* (Hardgraft and Guv. Editors, Marcel Dekker, 247–291, 1989).

Cleary, Gary W., "Transdermal Controlled Release Systems," *Medical Applications of Controlled Release* (Langer and Wise, Editors, CRCPress 203–251, 1984).

Clegg and Vaz, "Translational diffusion of proteins and lipids in artificial lipid bilayer membranes. A comparison of experiment with theory," *Progress in Protein–Lipid Interactions Watts*, ed. (Elsvier, NY 1985) Chapter 5:173–229.

Davis, J. et al., "Characterization of Recombinant Human Erythropoietin Produced in Chinese Hamster Ovary Cells," *Biochemistry* 26:2633–2638 (1987).

Ebert, et al., "Transbuccal Absorption of Diclofenac Sodium in a Dog Model," *Controlled Release Technology Pharmaceutical Application* (Lee, et al. Editors, American Chemical Society)310–321 (1987).

Eggerth, et al., "Evaluation of Hamster Cheek Pouch as a Model for Buccal Absorption," *Proceed. Intern. Symp. Rel. Bioact. Mater.,* (Controlled Release Society, Inc.) 14:1809–181 (1987).

D'Emanuele, et al., "An Investigation of the Effects of Ultrasound on Degradable Polyanhydride Matrices," *Macromolecules* 25:511–515 (1992).

Elias, "The Microscopic Structure of the Epidermis and Its Derivatives," *Percutaneous Absorption: Mechanisms–Methodology–Drag Delivery* (Bronaugh, R.L., Maibach, H., Editors, Marcel Dekker, New York,) 1–12 (1989).

Flynn, G. L., "Mechanism of Percutaneous Absorption from Physiochemical Evidence," *Percutaneous Absorption: Mechanisms–Methodology–Drug Delivery* (Bronaugh, R.L., Maibach, H., Editors, Marcel Dekker, New York) 27–51 (1989).

Friedman, R. M., *Interferons: A Primer,*(Academic Press, New York, 1981).

Gaetner, W., "Frequency Dependence of Ultrasonic Cavitation," *J. Acoust. Soc. Am.* 26:977–980 (1954).

Ghanem et al., "The effects of ethanol on the transport of lipophilic and polar permeants across hairless mouse skin: Mehtods/validation of a novel approach," *Int. J. Pharm.* 78:137–156 (1992).

Grups and Frohmuller, "Cyclic Interferon Gamma Treatment of Patients with Metastic Renal Carcinoma," *J. Med.* 64(3):218–220 (1989).

Hansch and Leo, "Substituent Constants for Correlation Analysis in Chemistry and Biology" (1979).

Junginger, et al., "Visualization of Drug Transport Across Human Skin and the Influence of Penetration Enhancers," *Drug Permeation Enhancement* (Hsieh, D.S., Editors, Marcel Dekker, Inc. New York) 59–89 (1994).

Kasting, et al., "Prodrugs for Dermal Delivery: Solubility, Molecular Size, and Functional Group Effects," Prodrugs: Topical and Ocular Delivery Sloan, ed. (Marcel Dekker, NY 1992) 117–161.

Kost and Langer, "Ultrasound–Mediated Transdermal Drug Delivery," *Topical Drug Bioavailability Bioequivalence and Penetration* (Maibach, H.I., Shah, V.P., Editors, Plenum Press, New York) 91–104 (1993).

Kost, et al., "Ultrasound Effect on Transdermal Drug Delivery," (Ben Gurion University Dept. of Chem. Engineering, Beer Sheva Israel) (MIT, Dept. of Applied Biological Sciences, Cambridge, MA) CRS Aug. 1986.

Krall, L.P., World Book of Diabetes in Practice (Editors, Elsvier, 1988).

Lee, V. H. L., et al., "Protease Inhibition as an Additional Mechanism for the Nasal Absorption Enhancement Effect of Sodium Taurodihydrofusidate," *Proceed. Intern. Symp. Control Rel. Bioact. Mater* 14:55–56 (1987).

Lee, V. H. L., et al., "Nasal Peptide and Protein Absorption Promoters: Aminopeptides Inhibition as a Predictor of Absorption Enhancement Potency of Bile Salts," *Proceed. Intern. Symp. Control Rel. Bioact. Mater* 14:53–54 (1987).

Levy, et al., "Effect of Ultrasound on Transdermal Drug Delivery to Rats and Guinea Pigs," *J. Clin. Invest.* k 83:2074–2078 (1989).

Liu, et al., "Cotransport of Estradiol and Ethanol Through Humsn Skin In Vitro: Understanding the Permeant/Enhancer Flux Relationship," *Pharmaceutical Research* 8:938–944 (1991).

Liu, et al., "Experimental Approach To Elucidate the Mechanism of Ultrasound–Enhanced Polymer Erosin and Release of Incorporateed Substances," *Macromolecules* 25:123–128 (1992).

Machluf and Kost, "Ultrasonically enhanced transdermal drug delivery. Experimental approaches to elucidate the mechansim," *J. Biomater. Sci. Polymer Edn.* 5:147–156 (1993).

Malk, et al., "Oleic Acid Concentration and Effect in Human Stratum Corneum: Non–Invasive Determination by Attenuated Total Reflectance Infrared Spectroscopy In Vivo," *J. Controlled Res.* 12:67–75 (1990).

Mitragotri, et al., "Ultrasound–Mediated Transdermal Protein Delivery," *Science* 269:850–853 (1995).

Mitragotri, et al., "A Mechanism Study of Ultrasonic–Enhanced Transdermal Drug Delivery," *J. Pharm. Sci.* 84:697–706 (1995).

Mitragotri, et al., *In. Encl. of Pharm Tech.*: Swarbrick and Bovian, Ed., Marcel Dekker (1995)*.

Morimoto, Y., et al., "Prediction of Skin Permeability of Drugs: Comparison of Human and Hairless Rat Skin," *J. Pharm. Pharmacol.* 44:634–639 (1991).

Nagai and Konishi, "buccaal/Gingival Drug Delivery Systems," *Journal of Controlled Release* (Elsevier Science Publishers B.V., Amsterdam) 6:353–360 (1987).

Newman, J., et al., "Hydrocortison Phonophoresis," *J. Am. Ped. Assoc.* 82:432–435 (1992).

Olanoff and Gibson, "Method to Enhance Intranasal Peptide Delivery," *Controlled Release Technology Pharmaceutical Application* (Lee, et al. Editors, American Chemcial Society)301–309 (1987).

Ongpipattanankul, et al., "Evidence the Oleic Acid Exists in a Separate Phase Within Stratum Corneum Lipids," *Pharm. Res.* 8:350–354 (1991).

Parkin, et al., "Atropic manifestations in the acquired immune deficiency syndrome: response to recombinant interferon gamma," *Br. Med. J.,* 294:1185–1186 (1987).

Perry, et al., "Perry's Chemical Engineering Handbook" (McGraw–Hill, NY 1984).

Pishko, et al., "Amperometric Glucose Microelectrodes Prepared through Immobilzation of Glucose Oxidase in Redox Hydrogels," *Anal. Chem.* 63:2268–2272 (1991).

Potts and Guy, "Predicting Skin Permeability," *Pharm. Res.* 9:663–669 (1992).

Prausnitz, et al., "Electroporation of mammalian skin: A mechanism to enhance transdermal drug delivery," *Proc. Natl. Acad. Sci. USA* 90:10504–10508 (1993).

Quillen, W.S., "Phonophoresis: A Review of the Literature and Technique," *Athl. Train.* 15:109–110 (1980).

Robinson & Lee, "Influence of Drug Properties on Design," *Controlled Drug Delivery* 42–43.

Rosell, J., et al., "Skin Impedance From 1 Hz to 1mHz," *IEEE Trans. Biomed. Eng.* 35:649–651 (1988).

Skauen, et al., "Phonophoresis," *Int. J. Pharm.* 20:235–245 (1984).

Stringfellow, *Clinical Applications of interferons and their inducers,* (Editors, Marcel Dekker, New York, 1986).

Tamada, et al., *Proceed. Intern. Symp. Control. Rel. Bioact. Mater*, 22, 129–130 (1995).

Tocanne, et al., "Lipid lateral diffusion and membrane organization," *FEB* 257:10–16 (1989).

Tyle and Agrawala, "Drug Delivery by Phonophoresis," *Pharm. Res.* 6:355–361 (1989).

Veilalrd, et al., "Buccal Controlled Delivery of Peptides," *Proceed. Intern. Symp. Control. Rel. Bioact. Mater. (Controlled Release Society, Inc.)* 14:6 (1987).

Walker and Hadgraft, "Oleic acid—a membrane 'fluidiser' or fluid within the membrane," *Int. J. Pharm.* 71:R1–R4 (1991).

Walmsley, "Application of Ultrasound in Dentistry," *Ultrasound in Med. and Biol.* 14:7–14 (1988).

Walters, K. A., "Penetration Enhancers and Their Use in Transdermal Therapeutics Systems," *Transdermal Drug Delivery: Developmental Issues and Research Initiatives,* 197–246 (Hadgraft J., Guy, R.H., Editors, Marcel Dekker, 1989).

Wester and Mailbach, "Animal Models for Percutaneous Absorption," *Topical Drug Bioavailability Bioequivalence and Penetration* (Shah and Maibach, Editors, Plenum Press, New York) 333–349, (1993).

Wheatley, et al., "Use of Ussing Chamber for Investigation of Drug Delivery Across Viable Nasal Tissue Membranes," *Proceed. Intern. Symp. Control Rel. Bioact. Mater.* (Controlled Release Society, Inc. 14:26–27 (1987).

Williams, et al., "On the non–Gaussian distribution of human skin permeabilities," *Int. J. Pharm.* 86:69–77 (1992).

Wilschut, et al., "Estimating Skin Permeation, The Validation of Five Mathematical Skin Permeation Models," *Chemosphere* 30:1275–1296 (1995).

TRANSDERMAL PROTEIN DELIVERY USING LOW-FREQUENCY SONOPHORESIS

The United States government has rights in this invention by virtue of NIH grant GM44884 to R. Langer.

BACKGROUND OF THE INVENTION

The present invention is generally in the area of drug delivery, and is particularly an improved method for transdermal drug delivery.

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, In *Percutaneous Absorption: Mechanisms-Methodology-Drag Delivery.*, Bronaugh, R. L., Maibach, H. 1. (Ed), pp 1–12, Marcel Dekker, New York, 1989. The word "transdermal" is used herein as a generic term. However, in actuality, transport of drugs occurs only across the epidermis where the drug gets absorbed in the blood capillaries. When compared to injections, TDD eliminates the associated pain and the possibility of infection. Theoretically, the transdermal route of drug administration could be advantageous in the delivery of many therapeutic proteins, because proteins are susceptible to gastrointestinal degradation and exhibit poor gastrointestinal uptake, proteins such as interferons are cleared rapidly from the blood and need to be delivered at a sustained rate in order to maintain their blood concentration at a high value, and transdermal devices are easier to use than injections.

In spite of these advantages, very few drugs and no proteins or peptides are currently administered transdermally for clinical applications because of the low skin permeability to drugs. This low permeability is attributed to the stratum corneum (SC), the outermost skin layer which consists of flat, dead cells filled with keratin fibers (keratinocytes) surrounded by lipid bilayers. The highly-ordered structure of the lipid bilayers confers an impermeable character to the SC (Flynn, G. L., In *Percutaneous Absorption: Mechanisms-Methodology-Drug Delivery.*; Bronaugh, R. L., Maibach, H. I. (Ed), pages 27–53, Marcel Dekker, New York, 1989). Several methods, which include chemical enhancers (Burnette, R. R. In *Developmental Issues and Research Initiatives*; Hadgraft J., G., R. H., Eds., Marcel Dekker: 1989; pp. 247–288) and electricity (Prausnitz *Proc. Natl. Acad. Sci. USA* 90, 10504–10508 (1993); Walters, K. A., in *Transdermal Drug Delivery: Developmental Issues and Research Initiatives*, Ed. Hadgraft J., Guy, R. H., Marcel Dekker, 1989), have been proposed to enhance transdermal drug transport. However, the efficacy of these methods in enhancing transdermal protein transport has been limited by the large protein size and relatively low electric charge on the proteins.

Ultrasound has been shown to enhance transdermal transport of low-molecular weight drugs (molecular weight less than 500) across human skin, a phenomenon referred to as sonophoresis (Levy, J. Clin Invest. 1989, 83, 2974–2078; Langer, R., In *"Topical Drug Bioavailability, Bioequivalence, and Penetration"*; pp. 91–103, Shah V. P., M. H. I., Eds. (Plenum: New York, 1993); Frideman, R. M., *'Interferons: A Primer'*, Academic Press, New York, 1981)). In a recent study of sonophoresis, it has been shown that application of ultrasound at therapeutic frequencies (1 MHz) induces growth and oscillations of air pockets present in the keratinocytes of the SC (a phenomenon known as cavitation). These oscillations disorganize the SC lipid bilayers thereby enhancing transdermal transport. However, application of therapeutic ultrasound does not induce transdermal transport of high-molecular weight proteins.

Transdermal drug delivery offers an advantageous alternative to oral delivery and injections. However, its applications are restricted to only a few drugs because of the extremely low skin permeability to drugs. A variety of approaches have been suggested to enhance transdermal transport of drugs. These include: i) use of chemicals to either modify the skin structure or to increase the drug concentration in the transdermal patch (Junginger, et al. In *"Drug Permeation Enhancement"*; Hsieh, D. S., Eds., pp. 59–90 (Marcel Dekker, Inc. New York 1994); ii) applications of electric fields to create transient transport pathways [electroporation] or to increase the mobility of charged drugs through the skin [iontophoresis], and iii) application of ultrasound [sonophoresis].

Sonophoresis has been shown to enhance transdermal transport of various drugs. Although a variety of ultrasound conditions have been used for sonophoresis, the most commonly used conditions correspond to the therapeutic ultrasound (frequency in the range of 1 MHz–3 MHz, and intensity in the range of 0–2 W/cm$^2$) (Kost, In Topical Drug Bioavailability Bioequivalence and Penetration, pp. 91–103, Maibach, H. I., Shah, V. P. (Ed) Plenum Press, New York, 1993; U.S. Pat. No. 4,767,402 to Kost, et al.). It is a common observation that the typical enhancement induced by therapeutic ultrasound is less than ten-fold. In many cases, no enhancement of transdermal drug transport has been observed upon ultrasound application. Accordingly, a better selection of ultrasound parameters is needed to induce a higher enhancement of transdermal drug transport by sonophoresis.

It is therefore an object of the present invention to provide an improved method for transdermal drug delivery.

It is a further object of the present invention to provide conditions for using sonophoresis for transdermal drug delivery.

SUMMARY OF THE INVENTION

Applications of low-frequency (20 KHz) ultrasound enhances transdermal transport of high-molecular weight proteins. This method includes a simultaneous application of ultrasound and protein on the skin surface in order to deliver therapeutic doses of proteins across the skin.

Examples demonstrate in vitro and in vivo administration of insulin (molecular weight 6,000 D), and in vitro administration of gamma interferon (molecular weight 17,000 D), and erythropoeitin (molecular weight 48,000 D).

BRIEF DESCRIPTION OF THE DRAWINGS

FIG. 2A is the blood glucose levels upon 1 hour insulin-ultrasound treatment (ultrasound was turned ON at 1 hour and turned OFF at 2 hours) at four different intensities (□—Control (n=4), ●—12.5 mW/cm$^2$ (n=3), ▲—62.5 mW/cm$^2$ (n=3), ◆—125 mW/cm$^2$ (n=3), and ■—225 mW/cm$^2$ (n=5)). FIG. 2B is a graph comparing the blood glucose level of rats treated for 1 hour (from time 1 to 2 hours) with sonophoresis at two intensities (▲—62.5 mW/cm$^2$ (n=3), ■—225 mW/cm$^2$ (n=5)) and those treated with a single subcutaneous injection at time 1 hour (dashed line—1 U (n=3), dotted line—100 mU (n=3). A typical rat weighed about 400 g. The control is indicated by (□) (error bars (SD) are shown on one set of data for subcutaneous as well as for sonophoresis data.) FIG. 2C is a graph of the time variation of blood glucose levels of hairless rats exposed to ultrasound (20 KHz, 225 mW/cm$^2$, 100 msec pulses applied every second) for different exposure times. Ultrasound was turned ON at 1 hour (indicated by the arrow) and was turned OFF after: 1 minute (●) (n=3), 10 minutes (▲) (n=3), and 1 hour (■) (n=5). The control is indicated by (□) (error bars (SD) are shown on one set of data). FIG. 2D is a graph of the time variation of blood glucose levels of diabetic hairless rats upon a 30 minute insulin-ultrasound treatment (ultrasound was turned ON at 0.5 hour and turned OFF at 1 hour). (0—Diabetic Rats, Δ—Normal Rats, ▲—Diabetic Rats with insulin-ultrasound treatment.) (n=4 per experiment, error bars indicate SD).

DETAILED DESCRIPTION OF THE INVENTION

Figure 1A:
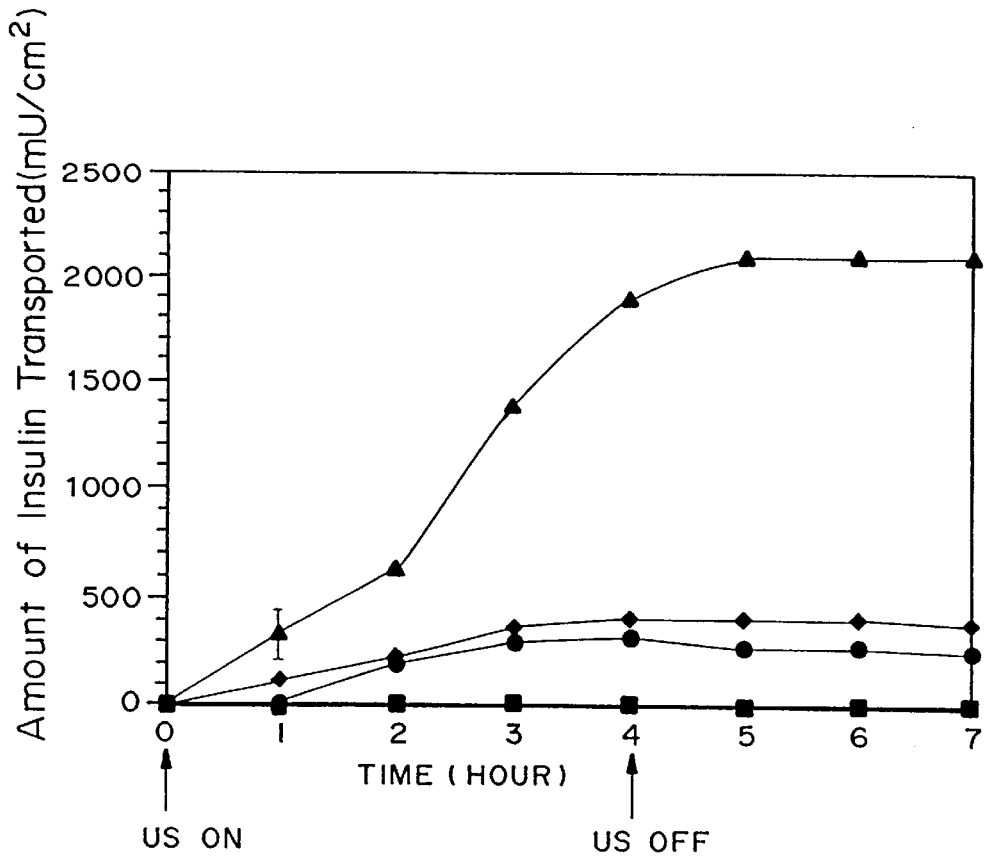
FIG. 1A is a graph of the amount of insulin transported across human skin (in vitro) in the presence of ultrasound (20 KHz, 100 msec pulses applied every second) at various intensities (■—12.5 mW/cm$^2$, ♦—62.5 mW/cm$^2$, ●—125 mW/cm$^2$, and ▲—225 mW/cm$^2$). (n=3–4, error bars indicate SD (Standard Deviation))

Sonophoresis:

As used herein, sonophoresis is the application of ultrasound to the skin on which a drug, most preferably proteinaceous in nature, alone or in combination with a carrier, penetration enhancer, lubricant, or other pharmaceutically acceptable agent for application to the skin, has been applied. As used herein, "low frequency" sonophoresis is ultrasound at a frequency that is less than 1 MHz, more typically in the range of 20 to 40 KHz, which is preferably applied in pulses, for example, 100 msec pulses every second at intensities in the range of between zero and 1 W/cm$^2$, more typically between 12.5 mW/cm$^2$ and 225 mW/cm$^2$.

Many ultrasound devices are available commercially which can be used in the method described herein. For example, the ultrasonic devices used by dentists to clean teeth have a frequency of between about 25 and 40 KHz. Commercially available portable ultrasound tooth-brushes make use of a small sonicator contained within the toothbrush (Sonex International Corporation). This sonicator is portable and operates on rechargeable batteries. Small pocket-size sonicators carried by patients and used to "inject" drugs whenever required could be readily adapted from these devices. In addition, these devices could be potentially combined with sensors that can monitor drug concentrations in the blood to formulate a self-controlled drug (insulin, for example) delivery method that can potentially eliminate the attention required by the patient.

Devices typically used for therapeutic or diagnostic ultrasound operate at a frequency of between 1.6 and 10 MHz. These devices can also be modified for use at lower frequencies.

Drugs to be Administered.

Drugs to be administered include a variety of bioactive agents, but are preferably proteins or peptides. Specific examples include insulin, erythropoietin, and interferon. Other materials, including nucleic acid molecules such as antisense and genes encoding therapeutic proteins, synthetic organic and inorganic molecules including antiinflammatories, antivirals, antifungals, antibiotics, local anesthetics, and saccharides, can also be administered.

The drug will typically be administered in an appropriate pharmaceutically acceptable carrier having an absorption coefficient similar to water, such as an aqueous gel. Alternatively, a transdermal patch such as the one described in the examples can be used as a carrier. Drug can be administered in a gel, ointment, lotion, suspension or patch, which can incorporate anyone of the foregoing.

Administration of Drug

The drug is preferably administered to the skin at a site selected based on convenience to the patient as well as maximum drug penetration. For example, the arm, thigh, or stomach represent areas of relatively thin skin and high surface area, while the hands and feet are uneven and calloused. In the preferred embodiment, drug is applied to the site and ultrasound applied immediately thereafter.

Based on these calculations and the data in the following examples, one can calculate the required dosage and application regime for treatment of a patient, as follows. A typical diabetic patient (70 Kg weight) takes about 12 Units of insulin three times a day (total dose of about 36 Units per day: cited in 'World Book of Diabetes in Practice' Krall, L. P. (Ed), Elsvier, 1988). If each insulin dose was to be delivered by sonophoresis in 1 hour, the required transdermal flux would be 12 U/hour. Note that 1 unit (1 U) of insulin corresponds approximately to 40 mg of insulin. The transdermal patch area used in these calculations is 40 cm$^2$ (the area of a transdermal Fentanyl patch [ALZA Corporation]). The donor concentrations used in these calculations are 100 U/ml in the case of insulin (commercially available insulin solution [Humulin]), $3 \times 10^7$ in the case of γ-interferon (typical concentration of interferon solution recommended by Genzyme Corporation), and $3 \times 10^5$ U/ml in the case of erythropoeitin [Davis J., Arakawa T., Strickland T., Yphantis D., Biochemistry, 2633–2638, 1987].

A typical γ-interferon dose given each time to patients suffering from cancer or viral infections is about $5 \times 10^6$ U [(i) Grups J. W., Frohmuller H. G., Br. J. Med., 1989, 64 (3): 218–220, (ii) Parkin J. M., Eales L., Galazka A., Pinching A., Br. Med. J., 1987, 294: 1185–1186.] Similar doses of αinterferon and β-interferon have also been shown to enhance the immune response of patients suffering from viral infections and cancer (cited in 'Clinical Applications of interferons and their inducers', Ed. Stringfellow D., Marcel Dekker, New York, 1986). If this interferon dose was to be given by sonophoresis in 1 hour, the required transdermal flux would be $5 \times 10^6$ U/hour. Note that 1 unit of γ-interferon corresponds approximately to 1 pg of γ-interferon.

A typical daily erythropoeitin dose given subcutaneously to anemic patients is about 400 U (cited in 'Subcutaneous Erythropoeitin, Bommer J., Ritz E., Weinreich T., Bommer G., Ziegler T., Lancet, 406, 1988). If this dose was to be delivered in three steps, each involving sonophoresis for 1 hour, the transdermal flux required would be about 140 U/hour. Note that 1 unit of erythropoeitin corresponds approximately to 7.6 nanograms of erythropoeitin.

An optimal selection of ultrasound parameters, such as frequency, pulse length, intensity, as well as of non-ultrasonic parameters, such as ultrasound coupling medium, can be conducted to ensure a safe and efficacious application using the guidelines disclosed herein as applied by one of ordinary skill in the art.

The present invention will be further understood by reference to the following non-limiting examples.

EXAMPLE 1
In Vitro Administration of Insulin

Materials and methods: In vivo as well as in vitro experiments were performed to study the effect of low-frequency ultrasound on the transport of insulin across the skin. In vitro experiments were performed using human cadaver skin. The skin was heat stripped by keeping it in water at 60° C. for two minutes followed by the removal of the epidermis. It was then stored at 4° C. in a humidified chamber. A piece of epidermis was taken out from the chamber prior to the experiments and was mounted on the Franz diffusion cell (Crown Bioscientific Co.) which consists of two compartments, the donor and the receiver compartment. A Franz Diffusion Cell consists of two compartments, a donor and a receiver compartment. The human cadaver epidermis (separated from the dermis by heat-treatment) is mounted between the two compartments and is supported by a Nylon mesh (Tetko Inc.) to avoid any damage. The skin was supported by a nylon mesh (Tetko Inc.) in order to a mimic the fact the skin in vivo is supported by mechanically strong dermis. The compartments were then clamped together. The receiver compartment was filled with 2% BSA (Sigma Chemicals) solution in PBS (Sigma Chemicals) and the donor solution was filled with 100 U/ml solution of human recombinant insulin (Humulin Regular). The ultrasound intensity, I, (Spatial Average Temporal Peak) was calculated from the values of the acoustic pressure amplitude, P, measured using a hydrophone (Bruel and Kjaer) using the equation, $I=P^2/2\rho c$, where $\rho$ is the water density (1 gm/ml), and c is the velocity of ultrasound in water [1500 m/s].

Ultrasound was turned ON at a frequency of 20 KHz, an intensity varying in the range of 0 to 1 $W/cm^2$ and 10% duty cycle. Samples (200 $\mu$l) were taken from the receiver compartment every hour to measure the concentration of insulin in the receiver compartment. The samples were immediately frozen and were stored at –20° C. till they were analyzed by RIA (Linco Research Co.). Ultrasound was typically applied for 4 hours and was then turned OFF. Transdermal insulin flux was followed for next two hours.

Figure 1B:
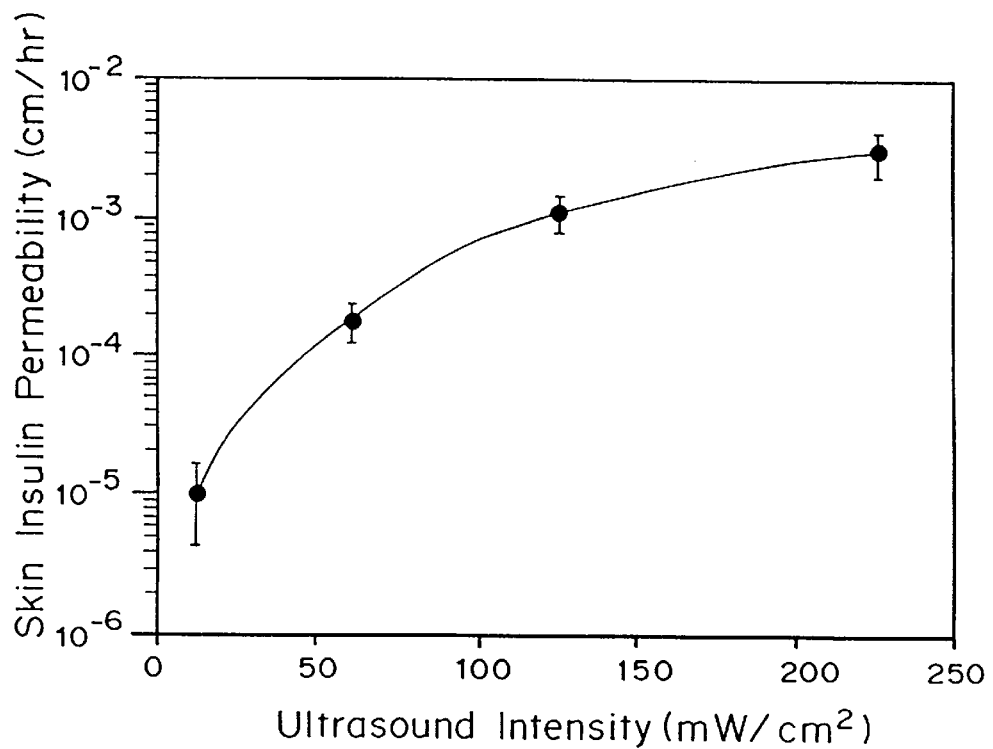
FIG. 1B is a graph of the variation of the transdermal insulin permeability (in vitro) with ultrasound intensity (20 KHz, 100 msec pulses applied every second). (n=3–4, error bars indicate SD.) Note that the skin is impermeable to insulin at an ultrasound intensity=○.

Results: The results are shown in FIGS. 1A and 1B and demonstrate that substantially greater transfer of protein through the skin occurs in the presence of ultrasound. FIGS. 1A and 1B show the variation of transdermal insulin flux across the human skin in vitro. Ultrasound (20 KHz, 125 $mW/cm^2$, 10%) was turned ON at time zero. The insulin flux increased from below the detection limit to a value of about 100 $mU/cm^2/hr$ in about 1 hour and stayed almost constant around that value as long as ultrasound was ON. Upon turning ultrasound OFF, the insulin flux decreases and achieves a value below our detection limit within 2 hours after turning ultrasound OFF. The skin permeabilities to insulin at various ultrasound intensities were calculated from the amount of insulin transported during the first hour of ultrasound exposure and are shown in FIG. 1B. The sonophoretic permeability varies nearly exponentially with ultrasound intensity, probably due to a highly nonlinear dependence of cavitation on ultrasound intensity (Apfel, R. E., *IEEE Trans. Ultrason. Ferroelectrics Freq. Control* 1986, UFFC-33, 139).

Application of ultrasound under these conditions did not appear to cause any permanent loss of the barrier properties of the skin. The transdermal insulin flux (proportional to the slope of the curves shown in FIG. 1A) three hours after turning ultrasound OFF was statistically insignificant. To further assess the recovery of the skin barrier properties after sonophoresis, water transport was measured through the skin during and after ultrasound exposure (20 KHz, 125 $mW/cm^2$, 100 msec pulses applied every second). Transdermal water transport was measured using the same set-up utilized in the insulin experiments, except that the donor compartment was filled with a 1 $\mu$Ci/ml solution of radio-labelled water ($^3$H). The concentration of water in the receiver compartment was measured using, a scintillation counter. During sonophoresis, a water permeability enhancement of 100-fold was observed, of which about 94 (±3) % was recovered within 2 hours after turning ultrasound OFF and 98 (±1) % was recovered within 15 hours. These results suggest that application of ultrasound does not induce any long-lasting loss of the skin barrier properties.

With a transdermal insulin flux of 100 $mU/cm^2/hr$, it should be possible to deliver therapeutic doses of insulin transdermally. Specifically, an insulin dose of about 13 U/h (a dose comparable to the estimated dose required by a diabetic patient if insulin is administered at a controlled rate) could be delivered from a patch having an area of 100 $cm^2$. Accordingly, ultrasound intensity should be useful to control transdermal insulin delivery.

EXAMPLE 2
In Vitro Transfer of Other Proteins

Methods and materials: The passive skin permeability to high-molecular weight proteins, including those mentioned above, is essentially zero (below the detection limit). To assess whether application of ultrasound enhances transdermal protein flux, the skin permeability to these proteins in the presence of ultrasound in vitro across human cadaver epidermis in a Franz Diffusion Cell (Crown Glass Company) was measured. In separate experiments, the donor compartment of the diffusion cell was filled with a solution of insulin (100 U/ml, Humulin Regular, Eli Lilly), γ-interferon (2500 U/ml, Genzyme Corp.), or erythropoeitin (400 U/ml, Amgen Corp.). Ultrasound (20 KHz, 100 msec pulses applied every second) was applied at intensities in the range of 12.5 $mW/cm^2$–225 $mW/cm^2$ for 4 hours using an ultrasound transducer (VCX 400, Sonics and Materials) which was immersed in the donor solution. The transducer having an area of about 1 $cm^2$ was oriented perpendicular to the skin and placed at a distance of 1 cm from the skin. The concentration of proteins in the receiver compartment was measured every hour either by RIA or ELISA. The insulin concentration in the receiver compartment was measured every hour by Radioimmuno Assay (performed at Linco Research Inc., St. Charles). The γ-interferon concentration was measured using ELISA methods developed by Endogen Inc, and the erythropoeitin concentration was measured by ELISA (performed at ARUP, Salt Lake City). Skin permeabilities to proteins were calculated using the transdermal fluxes measured during the first hour. The transdermal flux can be calculated using the equation, $J=\Delta M/\Delta t$, where $\Delta M$ is the amount of protein transported per unit skin area during time $\Delta t$. The skin permeabilities, P, can be calculated from the transdermal flux, J, during the first hour of ultrasound application using the equation, $P=J/\Delta C$, where $\Delta C$ is the concentration difference across the skin.

Results: Ultrasound application induces significant transdermal permeation of insulin, γ-interferon, and erythropoeitin. As demonstrated in Example 1, the human skin permeability at an ultrasound intensity of 225 $mW/cm^2$ is $3.3 \times 10^{-3}$ (±35%) cm/h to insulin. The permeability to γ-interferon under similar ultrasound conditions is $8 \times 10^{-4}$ (±22%) cm/h, and that to erythropoeitin is $9.8 \times 10^{-6}$ (±40%) cm/h. With these skin permeabilities, it should be possible to deliver these proteins transdermally at a therapeutically relevant rate. For example, one could deliver an insulin dose of about 12 U/h (a dose given three times a day to a diabetic patient) from a transdermal patch having an area of 40 cm² containing insulin at a concentration of 100 U/ml. In other words, one hour of sonophoresis performed three times a day could deliver the required daily dose of insulin to a diabetic patient. Similarly, a γ-interferon dose of about 5×10⁶ U/h (a daily dose required to enhance the immune response of patients suffering from viral infection or cancer), and an erythropoeitin dose of about 140 U/h (a dose that may be given three times a day to patients suffering from severe anemia) may be delivered from a similar patch by application of ultrasound. The ability of sonophoresis to deliver other macromolecules may be estimated based on their sonophoretic skin permeability which needs to be measured experimentally (generally decreases with increasing molecular size) and the required therapeutic dose of these macromolecules.

EXAMPLE 3
In Vivo Administration of Insulin

To assess the efficacy of ultrasound in enhancing transdermal flux in an in vivo model, insulin sonophoresis experiments were performed on hairless rats. The transport properties of hairless rat and hairless mouse skin have been shown to resemble those of human skin. The passive permeability of the hairless rat skin to many compounds is within a factor of 2–5 of the human skin permeability. (Morimoto, Y., Hatanaka, T., Sugibayashi, K., Omiya, H., *J. Pharm. Pharmacol.*, 44:634–639., Wester, R., Maibach, H. I., In Topical Drug Bioavailability Bioequivalence and Penetration, Maibach, H. I., Shah, V. P. (Ed) pages 333–347, Plenum Press, New York, 1993).

Materials and Methods: In vivo experiments were performed using hairless rats (Charles River). The rats were kept in quarantine to insure good health. On the day of experiment, they were taken out of the cages, anesthetized using a mixture of ketamine (90 mg/kg) and xylazine (10 mg/kg). After about an hour into anesthesia, a glass chamber was glued to the back of the rat using superglue (Permeabond). The glass chamber was filled with 100 U/ml solution of insulin and ultrasound (frequency of 20 KHz, intensity in the range of 0 to 1 W/cm², 100 msec pulses applied every second) was applied. The blood glucose level was measured every 30 minutes. Ultrasound was typically turned OFF after 1 hour, although the measurements of the blood glucose were continued for the next three hours.

The electrical resistance of the skin prior to each sonophoresis experiment was measured to ensure that the epidermis was not damaged. The epidermis is considered to be damaged if the initial specific epidermis resistance is less than 10 KΩ-cm² [Rossel J., Colominas J., Riu P, Pallas-Arery, Webster J., IEEE Trans. Biomed. Eng. 35: 649–651, 1988].

Histology samples from the area exposed to ultrasound were taken after the experiment was done and were stained using eosin and hematoxylin (Debora Heart and Lung Center). The histological studies of the hairless rat skin exposed to ultrasound were performed at Deborah Heart and Lung Institute, New Jersey. The skin samples, those exposed to ultrasound as well as those unexposed to ultrasound (controls), were stained with hematoxylin and eosin. These samples were later observed under a light microscope (40-fold magnification) to assess for possible structural damage. Five control skin samples and 20 skin samples exposed to ultrasound (5 samples corresponding to each ultrasound intensity in the range of 12.5 mW/cm² to 225 mW/cm²) were analyzed.

Results: Application of ultrasound (20 KHz, 125 mW/cm², 100 msec pulses applied every second) enhances insulin transport across the hairless rat skin in vivo. Simultaneous application of insulin and ultrasound decreases the blood glucose level of a diabetic rat from a high diabetic value (400 mg/dl) to the normal value (200 mg/dl) in 30 minutes.

Preliminary histological studies to assess the safety of low-frequency ultrasound as a transdermal transport enhancer were also conducted. The results indicated no damage to the skin as well as to the underlying parts of the skin exposed to ultrasound at an intensity up to 225 mW/cm².

Figure 2A:
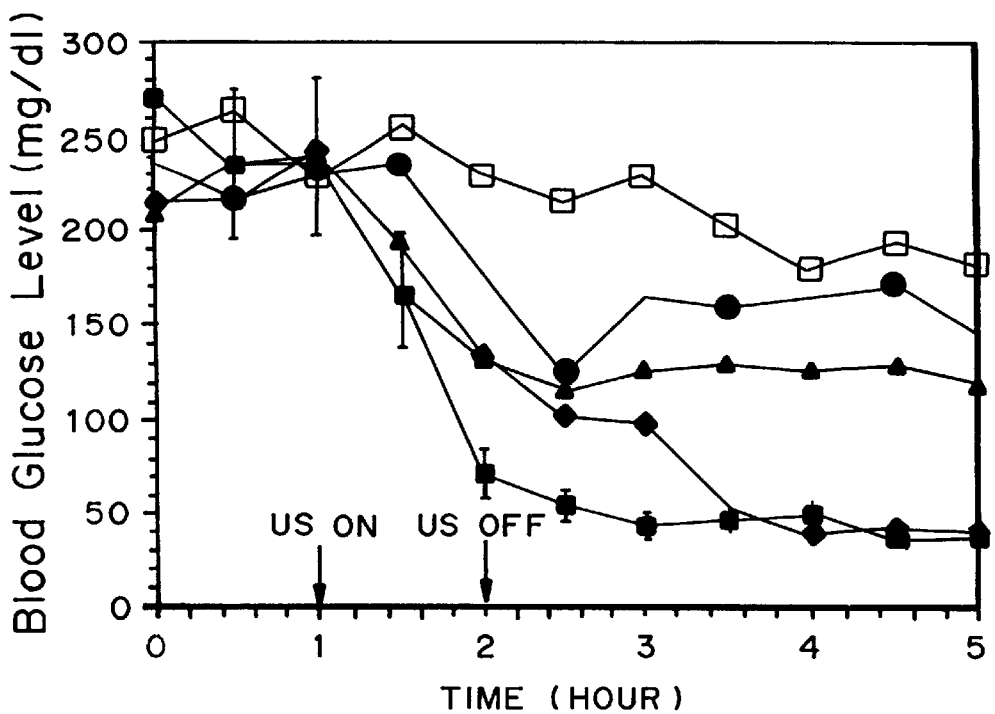
FIGS. 2A–2D are graphs of the time variance of the blood glucose levels of hairless rats (obtained from IFFA, Creto, France, generally about 16 weeks old at the time of the experiment).

FIG. 2A shows the blood glucose level of hairless rats upon a 1 hour insulin-ultrasound treatment (20 KHz, 100 msec pulses applied every second at intensities of 0 to 225 mW/cm². An intensity dependent decrease in the blood glucose level is observed upon ultrasound application, indicating that low-frequency sonophoresis can effectively deliver intensity-dependent insulin doses across hairless rat skin.

Figure 2B:
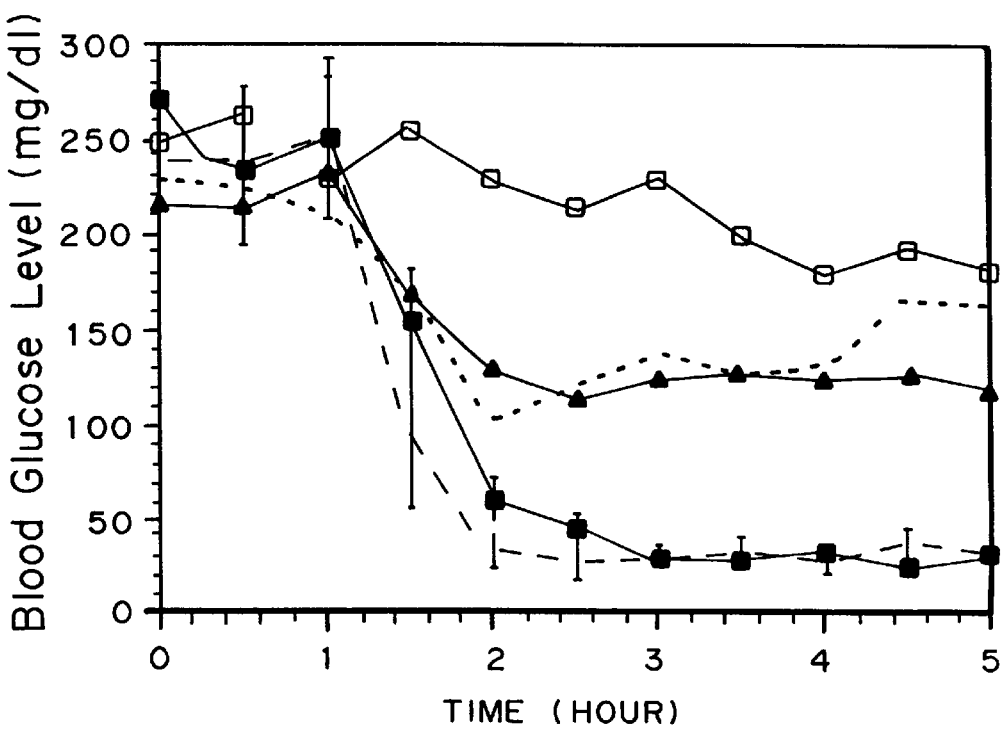

To estimate the amount of insulin penetrating the hairless rat skin during sonophoresis at the various intensities reported in FIG. 2A, various known amounts of insulin in the range of 0 to 1 U subcutaneously (most commonly used method of insulin administration today) in normal rats. The blood glucose levels of these rats were then compared with those of the normal rats undergoing sonophoresis. Subcutaneous injection of 100 mU and 1 U of insulin induced a decrease in the blood glucose level similar to that induced by sonophoresis using intensities of 62.5 mW/cm² and 225 mW/cm² respectively (see FIG. 2B). These results suggest that sonophoresis delivers intensity dependent insulin doses across the skin approximately in the range of 0 to 1 U (through an area of about 3 cm²).

Figure 2C:
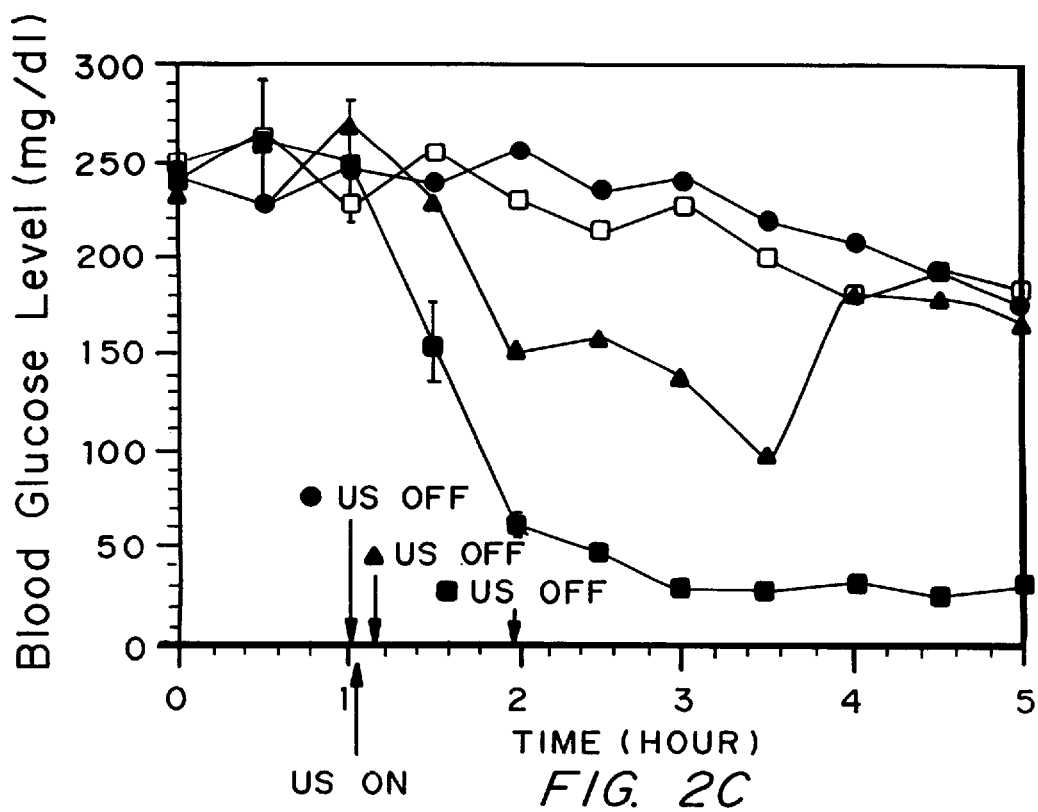

In order to estimate the dependence of the amount of insulin delivered on ultrasound exposure time (in vivo), insulin-sonophoresis experiments (20 KHz, 225 W/cm², 100 msec pulses applied every second) were performed on normal rats for different exposure times in the range of 1 minute to 1 hour. FIG. 2C shows that while a 1 hour exposure decreases blood glucose level from about 250 mg/dl to about 30 mg/dl, a 10 minute exposure to ultrasound reduces the blood glucose level of hairless rats from about 250 mg/dl to about 150 mg/dl. This result, when compared with the data reported in FIG. 2B, suggests that while a 1 hour ultrasound exposure delivers about 1 U of insulin, a 10 minute ultrasound application (225 mW/cm²) delivers about 100 mU through an area of 3 cm².

Figure 2D:
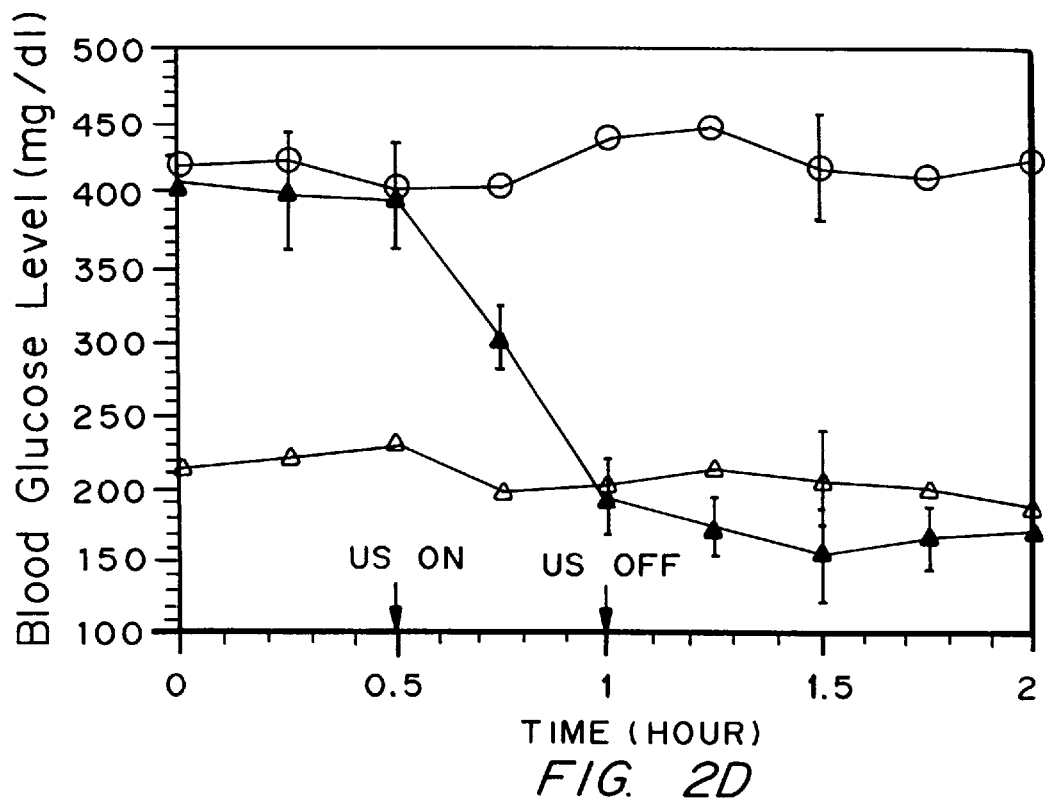

Additional experiments were performed to assess whether application of ultrasound can induce sufficient insulin transport across the skin of a diabetic hairless rat so that its blood glucose level becomes comparable to that of normal hairless rats. FIG. 2D shows blood glucose levels of diabetic rats during ultrasound-insulin treatment. Insulin-ultrasound treatment (20 KHz, 225 mW/cm², 100 msec pulses applied every second) reduces the blood glucose level of diabetic hairless rats from about 400 mg/dl to 200 mg/dl (the blood glucose level of normal rats) in 30 minutes. A corresponding change in the plasma insulin levels was observed during sonophoresis. Normal hairless rats were found to possess a plasma insulin level of 101±31 picomolar, while diabetic hairless rats were found to possess a value below the assay detection limit (34 picomolar). During sonophoresis, the levels of transdermally delivered human insulin in rat plasma reached a value of 77 (±28) picomolar after 30 minutes, and a value of 178 (±84) picomolar after 1 hour. No significant change in the plasma concentration of indigenous rat insulin was observed during sonophoresis.

The histology studies indicated no physical damage in the skin or in the underlying muscle tissues exposed to ultrasound at all the intensities used in the experiments described above. The regions of hairless rat's epidermis exposed to ultrasound were intact.

Modifications and variations of the method for transdermal drug delivery enhancement using sonophoresis described herein will be obvious to those skilled in the art and are intended to be encompassed by the following claims.

We claim:

1. A method for enhancing delivery of a drug in a single step across the skin into the blood using ultrasound wherein the ultrasound is applied by pulsing at a frequency of between 20 kHz and less than 1 MHz at an intensity not causing any irreversible skin damage for a period of time effective to deliver to the patient a therapeutic drug dosage into the blood.

2. The method of claim 1 wherein the drug is a peptide or protein.

3. The method of claim 1 wherein an effective amount of drug is administered in less than one hour.

4. The method of claim 1 wherein the frequency is between 20 and 45 kHz.

5. The method of claim 1 wherein the intensity is less than 1 W/cm$^2$.

6. The method of claim 5 wherein the intensity is between 12.5 mW/cm$^2$ and 225 mW/cm$^2$.

* * * * *